(12) United States Patent
Elliott

(10) Patent No.: US 6,316,248 B1
(45) Date of Patent: Nov. 13, 2001

(54) RAPID EXTRACTION OF HAIR ROOT DNA

(75) Inventor: James Elliott, Gloucester (CA)

(73) Assignee: Royal Canadian Mounted Police, Ottawa (CA)

( * ) Notice: Subject to any disclaimer, the term of this patent is extended or adjusted under 35 U.S.C. 154(b) by 0 days.

(21) Appl. No.: 09/695,249

(22) Filed: Oct. 25, 2000

(51) Int. Cl.$^7$ ................................ C12N 1/08; C12N 1/00
(52) U.S. Cl. ................................ 435/270; 435/243
(58) Field of Search ................ 536/25.4, 25.41, 536/25.42; 435/270, 243

(56) References Cited

U.S. PATENT DOCUMENTS 5,837,832 * 11/1998 Chee et al. .

OTHER PUBLICATIONS

Peter Savolainen et al. Forensic Evidence Based on ntDNA from Dog and Wolf hairs* Forensic Sci 1999 44(1):77–81.*
Alberts et al. Molecular Biology of the Cell Publisher+New York: Garland Publishing, Inc. 1994 pp:158–159.*
Thomas et al. Guide to Protein Purification Methods in Enzymology Publisher: San Diego: Academic press, Inc. 1990 vol. 182 pp:499–520.*

* cited by examiner

Primary Examiner—James Ketter
Assistant Examiner—Lisa Gansheroff
(74) Attorney, Agent, or Firm—George A. Seaby

(57) ABSTRACT

DNA-containing hair root cells are liberated from hair samples by soaking the hair root ends of the hair shafts in an aqueous solution consisting essentially of dithiothreitol, a surfactant such as sodium dodecylsulfate, a chelate such as ethylenediamine tetraacetic acid, an inorganic salt (NaCl), tris(hydroxymethyl) aminomethane and sufficient hydrochloric acid to make the pH of the solution approximately 8.

2 Claims, No Drawings

RAPID EXTRACTION OF HAIR ROOT DNA

BACKGROUND OF THE INVENTION

1. Field of the Invention

This invention relates to a method of extracting DNA-containing cells from hair roots.

2. Discussion of the Prior Art

Currently, so-called FTA (trademark) cards are used to collect and preserve samples of body fluid for subsequent DNA analysis. The cards, which are available from Fitzco, Inc., are described in detail in U.S. Pat. No. 5,496,562, which issued to L. A. Burgoyne on Mar. 5, 1996. Basically, the cards are defined by a cellulose based, solid matrix absorbent paper impregnated with a composition consisting of a surfactant (sodium dodecyl sulfate), a chelate (ethylenediame tetraacetic acid), a weak base tris (hydroxymethyl) aminomethane and optionally uric acid or a urate salt.

Blood DNA stored on FTA cards can be amplified in situ using polymerase chain reaction (PCR). FTA cards constitute a quick, safe and efficient method of purifying DNA for use in PCR without the need for quantitation. FTA cards were originally intended for use with blood only, but have been shown to be equally effective for saliva or buccal samples.

A third common source of DNA in forensics is hair roots. However, the liberation of hair root DNA into a liquid medium for spotting on FTA cards proved to be difficult and time consuming. The available methods (organic, Chelex and Qiagen®) all start by taking hair roots and using them directly to produce either double or single stranded DNA. Organic methods use organic solvents and DNA precipitation to isolate usable DNA. The methods require personal protection gear to protect the operators and quantitation of the DNA before use. Chelex methods render the DNA in a single strand format suitable for PCR, but are not always reliable. The Qiagen methods require expensive materials, are not amenable to automation and are expensive.

GENERAL DESCRIPTION OF THE INVENTION

The object of the present invention is to provide a quick and effective method for releasing hair root cells from the shaft of the hair for spotting on FTA cards.

Accordingly, the invention relates to a method of liberating DNA-containing hair root cells from a hair shaft comprising the steps of soaking a hair root end of the hair shaft in an aqueous solution of a sulfide bond breaking chemical, a surfactant, a chelate, an inorganic salt and sufficient buffer to render the solution slightly alkaline.

DESCRIPTION OF THE PREFERRED EMBODIMENT

More specifically, the invention relates to a method of liberating DNA-containing hair root cells from a hair shaft comprising the step of soaking a hair root end of the hair shaft in an aqueous solution consisting essentially of dithiothreitol for breaking sulfide bonds, the surfactant sodium dodecyl sulfate, the chelate ethylenediamine tetraacetic acid, sodium chloride tris(hydroxymethyl) aminomethane water, and sufficient hydrochloric acid to make the pH of the solution approximately 8.

Once the hair root DNA has been liberated into a liquid medium, it can be spotted onto FTA cards without interfering with the effectiveness of the FTA system.

The preferred formulation of the solution for liberating DNA-containing hair root cells consists of 1.23 g of dithriothreitol (DTT), 20 ml of 20% sodium diodecyl sulfate (SDS), 4 ml of sodium ethylenediame tetraacetic acid ($Na_2$ $EDTA.2H_2O$), 1.17 g of sodium chloride (NaCl), and 1.0 ml of 2.0 molar tris(hydroxymethyl) aminomethane (Tris) in sufficient water to bring the volume to 200 ml, and sufficient HCl to make the pH of the solution 8.0.

The solution is prepared by adding the Tris, the $Na_2$ EDTA $2H_2O$, the SDS and the NaCl to 160 ml of water, adding water to bring the volume to 200 ml, adjusting the pH of the solution to 8.0 using hydrochloric acid adding the DTT to the solution, and filter sterilizing the solution through a 0.22 $\mu$m filter. The resulting solution is divided into 6.0 ml aliquots and stored frozen at −20° C.

Different amounts and strengths of the solution were used to soak hair roots at 56° C. for 2–3 hours. The temperature can be varied by plus or minus five degrees. The hair shafts became soft and pliable, and it appeared that the hair root cells were liberated. A dye solution (40% sucrose and 0.025% bromophenol blue) was added to colour the fluid, which was pipetted onto FTA cards. 1.2 and 2 mm punches were taken and then purified as per normal FTA protocol. Optimization occurred.

Specifically, 40 $\mu$l of half strength solution was used to soak 2 and 4 proximal ends (hair root ends) from 10 individuals followed by amplification in 25 $\mu$l of one to three 1.2 mm FTA punches. In a second experiment, four roots of four individuals were soaked in 25 $\mu$l of solution, and one to three 1.2 mm FTA punches were amplified in 25 $\mu$l of solution. Finally, ten proximal ends from each of four individuals were soaked in 20 $\mu$l of solution to produce FTA stains, which were amplified using 15 $\mu$l and one to three 2 mm FTA punches.

The results were consistent with the observed amounts of hair root material on the hairs before processing. Different individuals will yield specific amounts of cellular material for a pulled hair root on a reasonably consistent basis, and the resulting PCR yields from the same number of processed roots are proportional.

Two individuals had strong cellular yield and two had poor cellular yield to the extent that there was no visible root with several of the hairs. The technique worked well, even with very little cellular material. Care must be taken at the start of the procedure to use an appropriate number of hair roots in an appropriate volume of solution to make the FTA stain, an appropriate area of the FTA stain must be purified (the correct number of 1.2 or 2 mm punches) and the "clean" punches must be amplified in the appropriate amplification volume. When these factors are gauged properly, unambiguous results are obtained.

I claim:

1. A method of liberating DNA-containing cells from hair shafts comprising the step of soaking the root ends of hair shafts in an aliquot of a solution consisting essentially of 1.23 g of dithiothreitol for breaking sulfide bonds, 20 ml of a 20% aqueous solution of sodium dodecyl sulfate, 4 ml of sodium ethylenediamine tetraacetic acid, 1.17g of sodium chloride, 1 ml of 2.0 molar tris(hydroxymethyl) aminomethane, sufficient water to bring the volume to 200 ml, and sufficient hydrochloric acid to make the pH of the solution 8.0, the soaking being effected for a time and at a temperature sufficient to liberate hair root cells.

2. The method of claim 1, wherein the soaking of the root ends is effected for 2–3 hours at 56°.

* * * * *